US012653485B2

(12) United States Patent
Gemmel et al.

(10) Patent No.: US 12,653,485 B2
(45) Date of Patent: Jun. 16, 2026

(54) MEASURING SYSTEM AND METHOD

(71) Applicant: Siemens Healthineers AG, Forchheim (DE)

(72) Inventors: Alexander Gemmel, Erlangen (DE); Riccardo Kunze, Erlangen (DE); Christoph Lötzsch, Pautzfeld (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 123 days.

(21) Appl. No.: 18/614,670

(22) Filed: Mar. 23, 2024

(65) Prior Publication Data

US 2025/0248676 A1     Aug. 7, 2025

(30) Foreign Application Priority Data

Mar. 23, 2023    (DE) ..................... 10 2023 202 610.4

(51) Int. Cl.
| | |
|---|---|
| *A61B 6/00* | (2024.01) |
| *A61B 6/58* | (2024.01) |
| *G01C 21/20* | (2006.01) |
| *G05D 1/244* | (2024.01) |
| *G05D 107/60* | (2024.01) |

(52) U.S. Cl.
CPC ............ *A61B 6/547* (2013.01); *A61B 6/4405* (2013.01); *A61B 6/582* (2013.01); *G01C 21/206* (2013.01); *G05D 1/244* (2024.01); *A61B 6/4441* (2013.01); *G05D 2107/65* (2024.01)

(58) Field of Classification Search
CPC .. G01C 15/002; G01C 15/02; G05D 2105/31; G05D 2109/10; G05D 2111/10; G05D 1/646; A61B 6/54
See application file for complete search history.

(56) References Cited

U.S. PATENT DOCUMENTS

| | | | | |
|---|---|---|---|---|
| 12,235,077 | B2 * | 2/2025 | Hughes | ..................... F41A 9/65 |
| 2017/0325647 | A1 * | 11/2017 | Kwak | ..................... A47L 9/009 |
| 2020/0302189 | A1 * | 9/2020 | Shu | ......................... G06V 10/82 |
| 2021/0146889 | A1 * | 5/2021 | Kuehne | ................ G05D 1/0225 |
| 2022/0057198 | A1 * | 2/2022 | Massie | .................. G01S 7/4026 |

(Continued)

FOREIGN PATENT DOCUMENTS

| | | | | | |
|---|---|---|---|---|---|
| CN | 103961098 | A | * | 8/2014 | .......... G05D 1/0234 |
| CN | 109074083 | A | * | 12/2018 | ............ B25J 13/089 |

(Continued)

*Primary Examiner* — Redhwan K Mawari

(74) *Attorney, Agent, or Firm* — Lempia Summerfield Katz LLC

(57) ABSTRACT

For a particularly precise check of travel accuracy, a measuring system is provided for checking and/or calibrating a travel accuracy of a mobile medical device that may be moved over a floor automatically or semiautomatically in a motorized manner. The measuring system includes a flat mat with an underside that may be arranged on the floor, and with an upper side on which indicator patterns that include at least one zero point mark for positioning the medical device and a number of track markings for travel motions of the mobile device are arranged. The measuring system includes a unit for illuminating the indicator patterns that are arranged on the mat using at least one concentrated light beam. The unit is arranged on the mobile medical device, such that the light beam is directed onto the upper side of the mat.

20 Claims, 9 Drawing Sheets

(56)                    References Cited

U.S. PATENT DOCUMENTS

| | | | | |
|---|---|---|---|---|
| 2023/0095366 A1 * | 3/2023 | Hollenborg | .......... | A61B 6/4476 |
| | | | | 378/198 |
| 2024/0310851 A1 * | 9/2024 | Ebrahimi Afrouzi | ... | G01S 17/87 |
| 2025/0223142 A1 * | 7/2025 | Le | .......... | G05D 1/693 |

FOREIGN PATENT DOCUMENTS

| | | | | | |
|---|---|---|---|---|---|
| CN | 110477718 A | * | 11/2019 | ............. | A47G 27/02 |
| CN | 211836262 U | * | 11/2020 | | |
| CN | 115047857 A | * | 9/2022 | .......... | G05D 1/0276 |
| DE | 102017007511 B3 | | 11/2018 | | |
| DE | 102021210771 A1 | | 3/2023 | | |
| DE | 102022107804 A1 | | 10/2023 | | |
| JP | 2010035981 A | * | 2/2010 | | |
| JP | 2015196600 A | * | 11/2015 | .......... | G05D 1/6445 |
| WO | WO-2016064093 A1 | * | 4/2016 | .......... | A47L 9/2852 |

* cited by examiner

MEASURING SYSTEM AND METHOD

This application claims the benefit of German Patent Application No. DE 10 2023 202 610.4, filed on Mar. 23, 2023, which is hereby incorporated by reference in its entirety.

BACKGROUND

The present embodiments relate to a measuring system for checking and/or calibrating a travel accuracy of a mobile medical device that may be moved over the floor in a motorized manner, and to a method for checking a travel accuracy of a mobile medical device that may be moved over the floor, using such a measuring system.

Independent of the grammatical term usage, individuals with male, female, or other gender identities are included within the term.

Mobile medical imaging devices (e.g., mobile C-arm x-ray devices) may have a C-arm with a recording system arranged thereon. The C-arm is arranged on a device cart. The C-arm or the holder thereof is equipped with drives in order to adjust the angle of inclination, for example, so that the recording system may be physically positioned in a number of projection directions. The device cart is equipped with wheels on which the mobile x-ray device may be manually moved. The wheels may be driven in a motorized manner in order to allow movement of the device cart with little or no physical effort and to automate specific motions of the mobile x-ray device for clinical applications. Modern mobile x-ray devices are deployed in many fields (e.g., for intraoperative imaging during operative procedures). In addition to simple projection images, mobile x-ray devices are also suitable for and may be deployed for 3D imaging or for panoramic imaging. For such deployments, for example, the device cart is to be positioned accurately and, for example, identically before each deployment, relative to the patient undergoing treatment.

Mobile C-arm x-ray devices having a motorized device cart are to be tested with respect to travel accuracy during manufacture, prior to delivery or following specific service deployments. For this purpose, an evaluation is made of the way in which the actual trajectory compares with a predetermined desired trajectory. For positional movements (e.g., movements to a predetermined desired point), it is possible, for example, to compare the difference between desired position and actual position. In the case of a Mecanum-based omnidirectional chassis, for example, deviations may occur in the two main directions x, y (e.g., according to the coordinate system of the mobile device, x, forwards/backwards, and y, sideways) and in chassis rotations $\phi$ (e.g., rotation about a chassis center).

In order to measure the accuracy of travel and/or motion, external tracking systems with cameras are used in the prior art. Alternatively, phantoms that are set up in the isocenter of the C-arm may be used.

SUMMARY AND DESCRIPTION

The scope of the present invention is defined solely by the appended claims and is not affected to any degree by the statements within this summary.

The present embodiments may obviate one or more of the drawbacks or limitations in the related art. For example, alternative measuring systems that allow simple and precise checking of a travel accuracy are provided. As another example, a method that performs a check is provided.

A measuring system of the present embodiments includes a flat mat with an underside that may be arranged on the floor, and with an upper side on which indicator patterns that include at least one zero point mark for positioning the medical device and a number of track markings for travel motions of the mobile device are provided. The measuring system also includes a unit for illuminating the indicator patterns that are arranged on the mat using at least one concentrated light beam. The unit is arranged on the mobile medical device (e.g., removably), such that the light beam is directed onto the upper side of the mat.

The flat mat may be laid on the floor such that a mobile device may be arranged thereon or adjacent thereto and, for example, move thereon. The indicator patterns are arranged on the upper side of the mat (e.g., as indentations or bulges or imprinted or impressed). The mat is used for an initial alignment of the mobile device in order to establish defined starting conditions. The illumination unit is attached to the mobile device using, for example, clamps, bolts, hook, and loop fastenings or a plug-in connection. The light beam of the illumination unit is then directed onto the mat and strikes the mat such that the light beam may be seen (e.g., in the form of a light dot or light spot, such as a visible light dot or light spot). The light beam may strike, for example, orthogonally in order to generate particularly reproducible conditions. The flat mat may be manufactured from, for example, plastic or rubber, or alternatively from carbon, metal, or natural fibers.

Using the measuring system of the present embodiments, the travel accuracy of the mobile device may be qualitatively and quantitatively verified in a manner that is simple, requires little effort, and is very precise, even by an inexperienced operator. This may be achieved, for example, by positioning and aligning the mobile device at the zero point mark (e.g., representing a cross pattern), then executing motions along the track markings. It is possible to monitor the motions by following the area of incidence (e.g., light dot or light spot) of the light beam on the flat mat. This may be performed manually by an operator (e.g., service technician) or (e.g., partly) automatically. The mat may be quickly packed away, transported, and laid out on the floor. The attachment of the illumination unit to the mobile device may be removable and may therefore likewise be arranged solely for the purpose of the check and then removed again. Further, it is also possible, using the measuring system, to perform a calibration of the travel accuracy by giving consideration to deviations from predeterminable distances and paths of travel. Resource-intensive checking of the travel accuracy using external tracking systems that are often expensive and occupy a considerable amount of space is not required. By virtue of the measuring system of the present embodiments, it is therefore possible to perform a check more frequently because the check may be done quickly between times. This provides greater resulting travel accuracy and, therefore, qualitatively improved imaging and better examinations.

According to an embodiment, the track markings include at least three travel lanes (e.g., two straight travel lanes arranged orthogonally relative to each other and one at least partly curved travel lane). Via the two reciprocally orthogonal travel lanes, the two main directions of the coordinate system x and y (e.g., forwards/backwards and sideways with corresponding positioning in relation to the wheels of the device cart) may be checked independently of each other with regard to the travel accuracy over at least one distance in each case, while a curved travel lane (e.g., in the form of an arc of a circle) is suitable for checking the travel accuracy with regard to rotations about a chassis center ($\phi$). In addition, one or more further travel lanes may be arranged on the mat (e.g., travel lanes that are arranged diagonally to the main directions and further straight or curved travel lanes of various lengths).

According to a further embodiment, the travel lanes include at least one start mark and one destination mark in each case. The travel accuracy may therefore be identified particularly easily and quickly (e.g., if a distance between start and destination is known and the mobile device is triggered to automatically cover the distance). During this activity, for example, the light beam is first directed at the start mark, and the position at which the light beam is situated is checked after the travel motion has ended. The respective destination mark may also be used as a start mark and vice versa. If a plurality of travel lanes of various lengths are superimposed (e.g., along the x-axis and y-axis), a plurality of destination marks may be required in order to identify this since the travel lanes are at least partly identical in this case.

According to a further embodiment, the indicator patterns contain coordinate system patterns and/or grid patterns and/or dimensional data and/or error region markings. Such patterns significantly aid a quantitative check or analysis of the travel accuracy. For example, it is possible, using error region markings (circles, squares, rectangles) around a destination mark, to establish at a glance whether or not the travel accuracy remains within a threshold value. Dimensional data and grid patterns such as, for example, scales (e.g., millimeter scales, degree scales, etc.) likewise significantly help an operator to see deviations. The display of a coordinate system may be used, for example, for simple and rapid positioning and orientation setting of the mobile device.

According to a further embodiment, the mat may be modularly assembled from at least two mat modules. Such a mat may be transported and stowed with particular ease. For example, the mat includes a number of mat modules that are shaped and may be assembled in the manner of a jigsaw puzzle. Such a jigsaw puzzle requires particularly little space when not in use, and may quickly be constructed when needed by virtue of the one-to-one assembly of a jigsaw puzzle. The alignment and orientation of the indicator patterns is likewise unambiguously predetermined and fixed by the jigsaw puzzle format, and therefore, nothing can slip.

For clear visual identification, the indicator patterns may be formed by dots and/or lines and/or circles and/or segments of a circle and/or rectangles. The indicator patterns may be identifiable solely by colors that differ from that of the mat (e.g., colored or black/white) or actually as a structural element that is distinguished from the rest of the mat, or both.

According to a further embodiment, the illumination unit takes the form of a laser. A laser is particularly long-lasting and provides the generation of a light spot or light dot that may be visually identified particularly clearly in the region of the area of incidence on the mat.

According to a further embodiment, the measuring system is also assigned a control unit with a control program for automatically triggering predetermined travel motions of the mobile device on the mat. The control unit may be part of the mobile device. The control program is loaded and stored thereon. In this case, the control program is configured to output control specifications for desired trajectories of the mobile device along the track markings of the mat (e.g., from the start mark to the destination mark of the respective travel lane and/or back), each desired trajectory being assigned to a travel lane. Some of the desired trajectories are, for example, linear travel motions in the previously cited main directions x, y, each being assigned to a corresponding linear travel lane. A travel lane may also be assigned a plurality of desired trajectories (e.g., there only or there and back). The length of the triggered desired trajectory corresponds in this case to, for example, the distance between the start mark and the destination mark of the respective travel lane. Some of the desired trajectories are, for example, curved travel motions about a radius (e.g., rotation about the track center/isocenter, PHI), and are assigned in each case to a curved travel lane. The length of the triggered desired trajectory in this case may likewise correspond to the distance between the start mark and the destination mark of the respective travel lane. Further, provision may also be made for additional specifications of further desired trajectories (e.g., travel motions along diagonal travel lanes), desired trajectories of various lengths, etc., these likewise being assigned to the corresponding travel lanes of the flat mat in each case. For example, the control specifications consist of pairs of desired trajectories, the second desired trajectory inverting the first desired trajectory, in order to measure both precision and accuracy of repetition.

According to a further embodiment, the measuring system includes a detection unit for detecting an actual position of the mobile device relative to the indicator patterns. If it is intended, in addition to or as an alternative to a manual check of the travel accuracy by an operator, to perform an automatic check with the aid of the measuring system, the detection unit may record, for example, the light beam or light dot or light spot of the illumination unit or the motion thereof relative to the indicator patterns. In order to achieve this, the detection unit may be a camera, for example, that is, for example, arranged together with the illumination unit in a holder. The holder may then be removably attached to the mobile device. In order to allow a particularly precise and rapid automatic check to be performed, the measuring system according to a further embodiment has an evaluation unit for evaluating the position, detected by the detection unit, of the mobile device relative to the indicator patterns, with respect to any deviation of an actual position from a desired position and/or with respect to any deviation of an actual trajectory from a desired trajectory. An automatic analysis of the travel accuracy is rapidly provided by this and may be fed back to the operator if necessary, or used subsequently for other purposes.

According to a further embodiment, an alignment unit that is arranged on the mobile device (e.g., a unit for generating a laser cross) is used to align the mobile device with the flat mat. Mobile x-ray devices generally have a unit for generating laser lines or a laser cross in order to visualize the isocenter. This alignment unit may likewise be used without effort to positionally align the mobile device (e.g., to position the mobile device and set the orientation). This may be performed, for example, with reference to the zero point mark or another indicator pattern of the flat mat. It is important here for the coordinate systems of the mobile device and the flat mat to be aligned with each other (e.g., congruent) in a defined manner.

According to a further embodiment, the mat has at least one recess. For example, the mat has at least two recesses that are arranged at defined intervals and are configured to allow the insertion of test elements for the purpose of checking interval sensors that are arranged on the mobile device. Mobile devices (e.g., mobile x-ray devices) that may be moved automatically often include a collision sensor system. For example, the publication DE 10 2021 210 771

A1 discloses a mobile x-ray device having a Lidar sensor that is arranged so as to scan at least part of the environment of the device cart and a device section. In order to calibrate such a collision sensor system, use may be made of, for example, two cuboids of defined shape and size. The cuboids are arranged at a precisely defined position and interval. Using the recesses arranged in the mat, the cuboids may very easily be arranged at precisely the correct position and orientation, and therefore, a rapid and simple calibration may be performed.

The present embodiments further include a method for automatically checking a travel accuracy of a mobile medical device that may be moved over the floor, using the measuring system described above and having the following acts: establishing a reproducible alignment of a coordinate system of the mat with a coordinate system of the mobile medical device by arranging the mobile medical device on the mat in a predefined position and orientation (e.g., with reference to the zero point mark); positioning the light beam emerging from the illumination unit such that the illumination unit illuminates a start mark or a destination mark; and triggering at least one desired trajectory using the control unit with the control program in order to move the mobile device along the travel lane that is assigned to the desired trajectory. Automating the further method includes the following acts: detecting the actual positions of the medical device relative to the indicator pattern at least at the end of the desired trajectory (e.g., also during the desired trajectory); evaluating the actual positions that have been detected (e.g., with respect to any deviation from a predetermined desired position, the deviation representing a measure of the travel accuracy of the device); and outputting a signal or an indication based on the evaluation.

According to a further embodiment, if a threshold value for a deviation is exceeded, a recalibration of the control unit with the control program is indicated and/or performed. In order to achieve this, it is also possible to specify correction values, for which purpose the deviations are quantitatively specified and taken into account.

DETAILED DESCRIPTION

Figure 1:
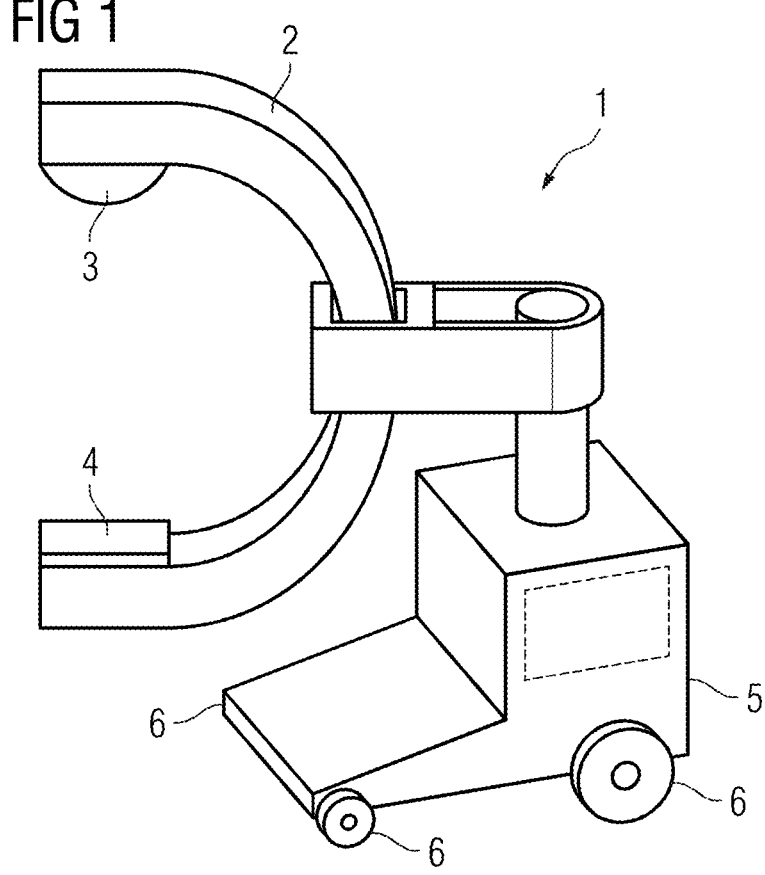
FIG. 1 shows a view of a medical mobile C-arm x-ray device.

FIG. 1 shows a conventional mobile medical C-arm x-ray device 1 that may be moved by motorized omnidirectional wheels 6. The mobile medical C-arm x-ray device 1 includes a C-arm 2 on which an x-ray source 4 and an x-ray detector 3 are arranged. The C-arm 2 is arranged on a device cart 5 that then includes the wheels 6. The C-arm x-ray device 1 is triggered by a control unit 14 (e.g., in relation to travel motions of the motorized wheels 6 on the floor). The travel motions may be triggered as desired (e.g., forwards/backwards, sideways (relating to the alignment of the wheels 6), in curves, etc.). The measuring system of the present embodiments includes at least a mat 7 (see FIGS. 2, 4, and 5) and an illumination unit 10 (see FIG. 3), is provided for the purpose of checking and, if necessary, calibrating quickly and with little effort the travel accuracy of such a mobile C-arm x-ray device 1 and generally any mobile medical device that may be moved in a motorized manner.

Figure 2:
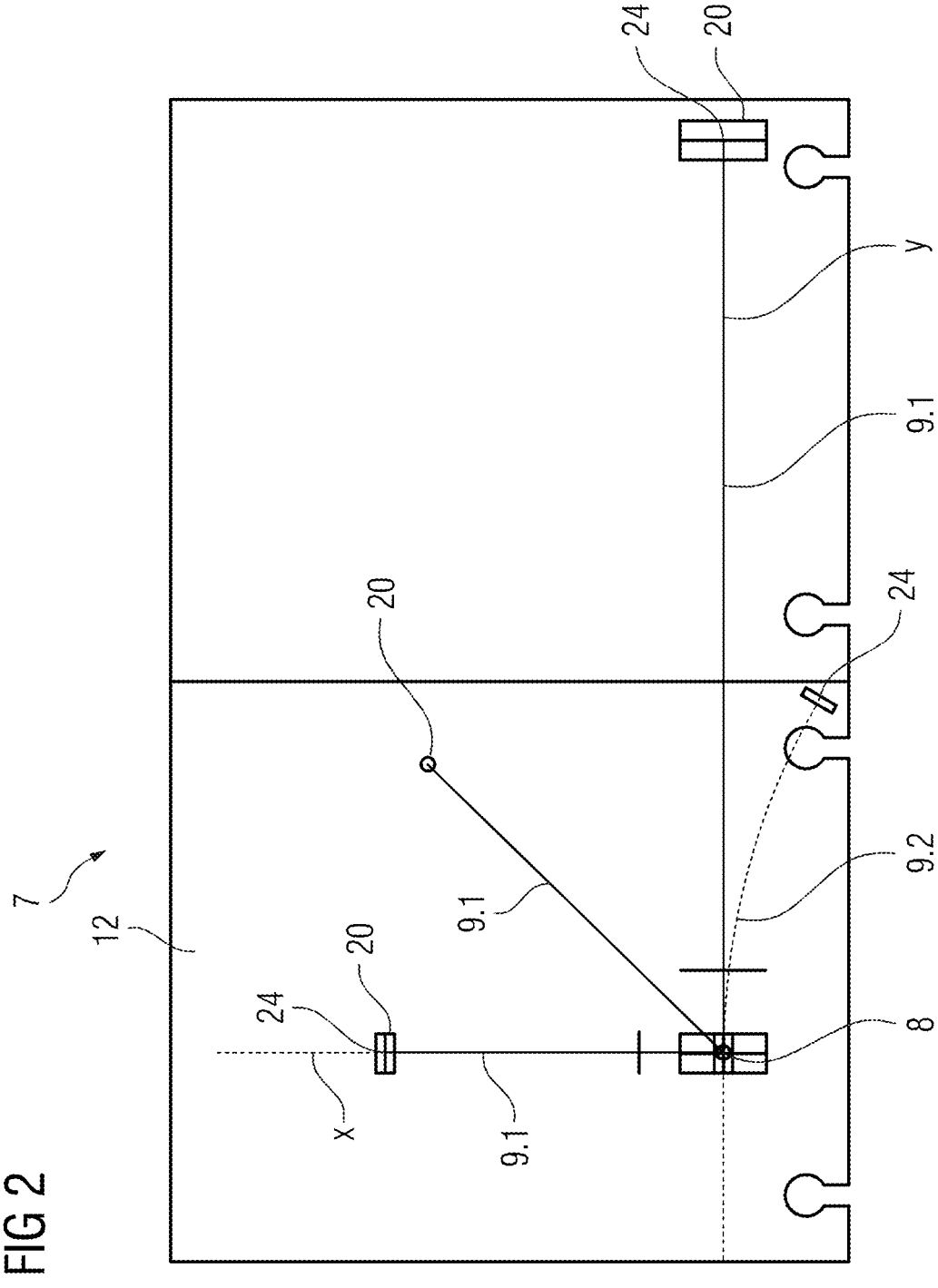
FIG. 2 shows an oblique plan view of an upper side of a mat as part of a measuring system for checking travel accuracy of a mobile device.

FIG. 2 shows a simple flat mat 7 having an underside (not visible) that may be arranged on the floor, and an upper side 12 with indicator patterns. The flat mat 7 is of modest height and is configured so as to be easily traversable by a mobile device without causing the device to tilt, even if only some of the, for example, four wheels are situated on the mat. The indicator patterns include a zero point mark 8 that serves as a starting point for positioning the mobile device. The zero point mark 8 may represent, for example, the zero point of a coordinate system having an x-axis x and a y-axis y, accordingly. In this way, the zero point mark 8 is configured as, for example, a cross. This is particularly suitable for positioning using a laser cross, as found on a typical C-arm x-ray device 1 for the purpose of visualizing the isocenter. The zero point mark 8 may also be configured as a start mark 23 and/or central point of a surrounding circle, square, or rectangle that may represent an error region 20 for the positioning.

The indicator patterns of the mat 7 also includes a number of track markings for travel motions of the mobile device. For example, at least two straight travel lanes 9.1 and one curved travel lane 9.2 are included, for example. The two straight travel lanes 9.1 are arranged orthogonally relative to each other, being formed at least partly by the x-axis x and the y-axis y of the coordinate system in the example shown. In this way, the zero point mark 8 forms the start point 23 of the straight travel lanes 9.1. In this case, the straight travel lanes 9.1 have, for example, a predetermined length, and the destination point 24 of the straight travel lane 9.1 is again surrounded by a circle or rectangle that indicates the error region 20. There may also be two or more destination points 24 at various distances from the start mark 23 (e.g., if a plurality of straight travel lanes 9.1 of various lengths (distance between start mark 23 and destination mark 24) are superimposed on each other).

In addition to the straight travel lanes 9.1 that are arranged along the x-axis x or y-axis y of the coordinate system, there may be further straight travel lanes (e.g., in the diagonal of the coordinate system as shown). The mat 7 also includes at least one curved travel lane 9.2 that likewise has its start point 23 at the zero point mark 8 and includes, for example, a partial arc of a circle. The curved travel lane 9.2 also has a destination point 24 that may likewise have an error region. Here again, a plurality of destination marks 24 may be present (e.g., a plurality of curved travel lanes 9.2 of various lengths (distance between start mark 23 and destination mark 24)). Various curved travel lanes 9.2 of various lengths and various radiuses may also be present. In one embodiment, all travel lanes may have their start point 23 at the zero point mark 8.

Dimensional data and grid patterns such as scales (e.g., millimeter scales, degree scales, etc.) may also be present on the mat 7 and also significantly help an operator to see deviations when monitoring the area of incidence of the light beam. The display of a coordinate system may be used, for example, for simple and rapid positioning and orientation setting of the mobile device.

The indicator patterns may be configured in various colors to allow greater clarity. The indicator patterns may be configured as continuous lines, dots, or dash-dot lines. The indicator patterns may be painted on, printed, impressed, etched, inscribed, or applied by other known methods, but may also be created already at the same time the mat 7 is manufactured. The color of the indicator patterns may also be configured to amplify light in order to aid the identification of the light spot.

Figure 4:
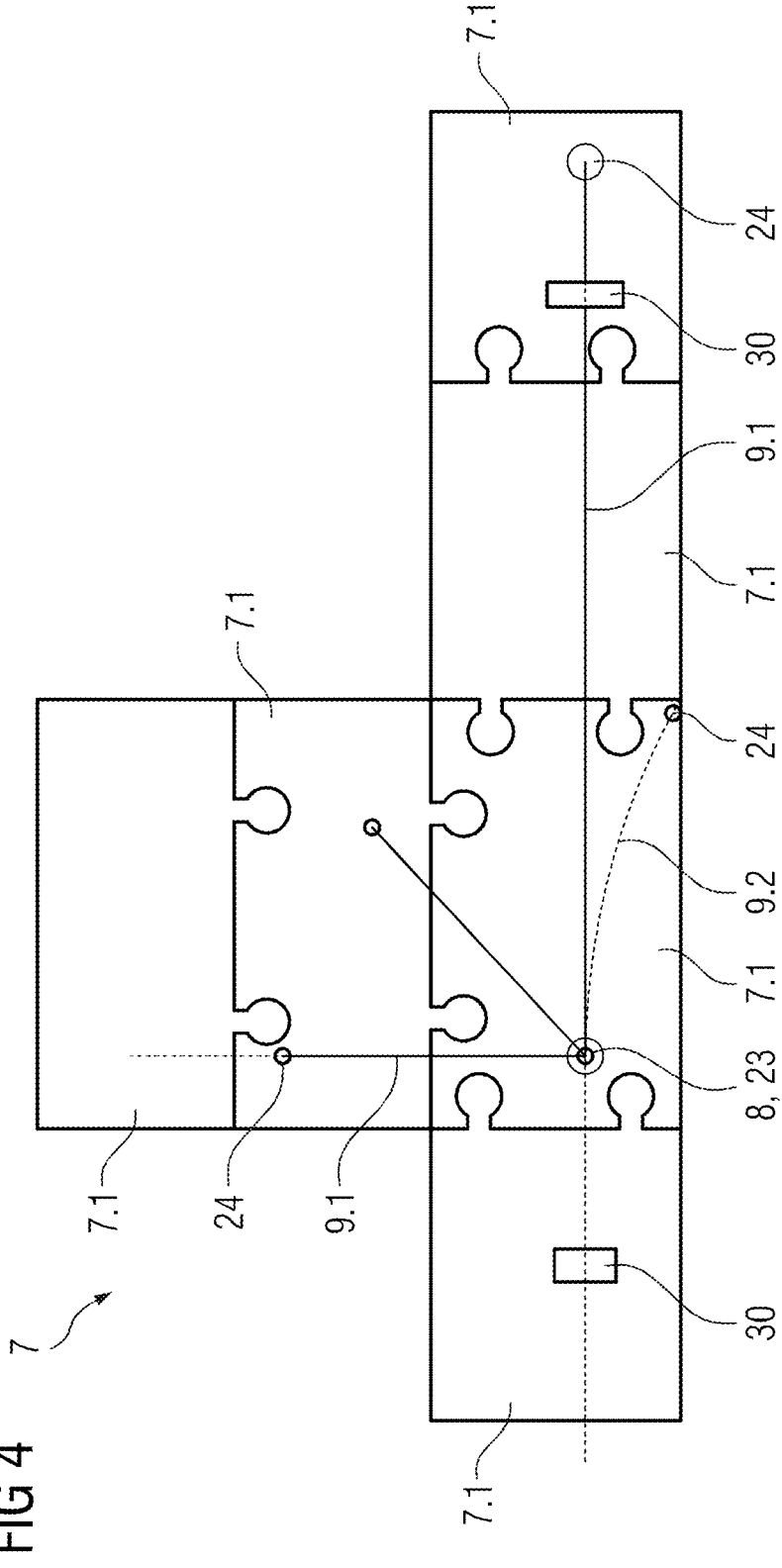
FIG. 4 shows an oblique plan view of an upper side of a modular mat.
Figure 5:
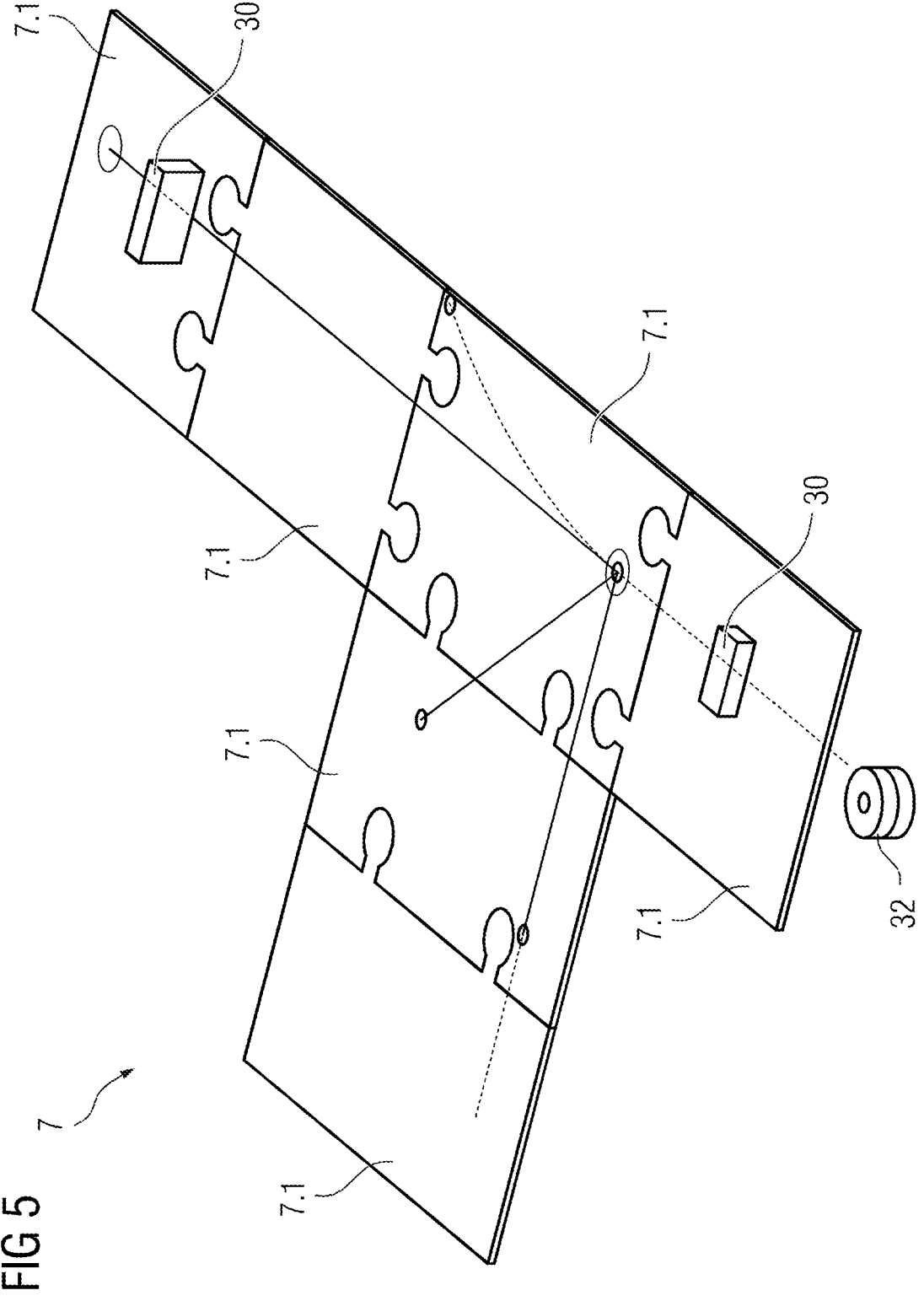
FIG. 5 shows a further oblique plan view of the upper side of a modular mat with test elements inserted into the recesses.

The flat mat 7 shown in FIG. 2 is configured as a single part, whereas modular flat mats 7 including a plurality of mat modules 7.1 are shown in FIGS. 4 and 5. The mat modules 7.1 are configured in the form of jigsaw puzzle parts and may be configured such that the mat modules 7.1 may only be assembled in one way. A one-to-one assembly of the modular mat 7 is thereby provided. The indicator patterns may extend over more than one mat module 7.1, such that, for example, the linear travel lane 9.1 that lies on the x-axis x extends over two partial mats 7.1 and the linear travel lane 9.1 that lies on the y-axis extends over three partial mats 7.1. The mat modules 7.1 may easily be put together, taken apart again, and packed up as required. In the example shown, the mat 7 has six mat modules 7.1 in total but may also be extended as required.

Figure 7:
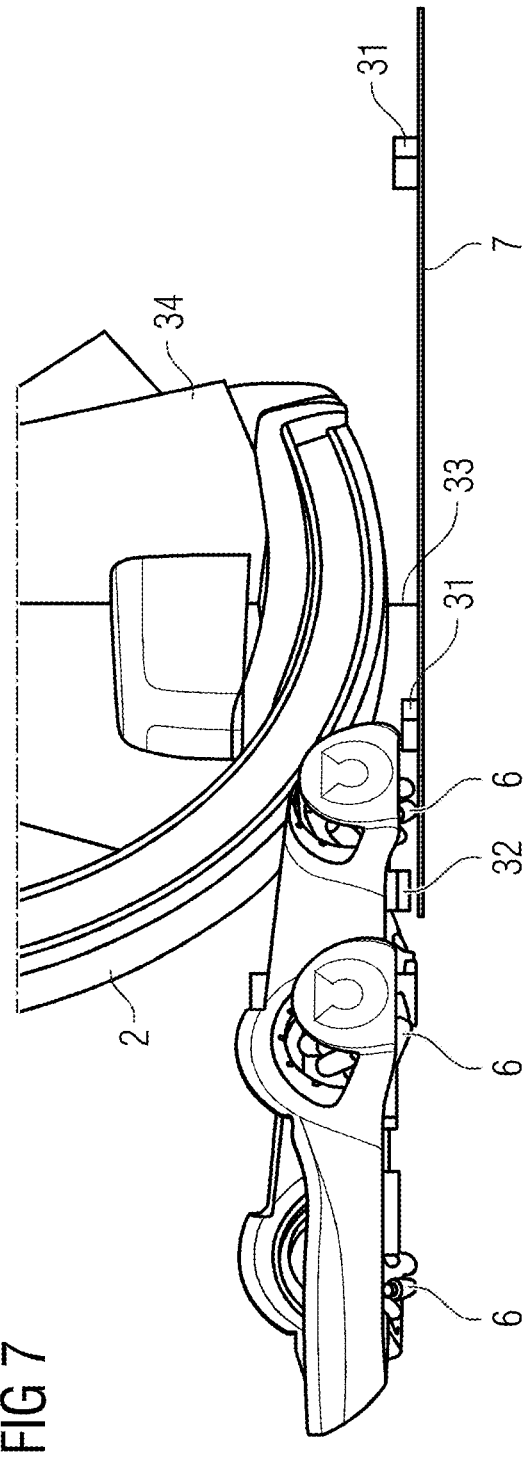
FIG. 7 shows a side view of a mat and a mobile C-arm x-ray device arranged partly on the mat.

The mat 7 also has two recesses 30 into which test elements 31 may be inserted as required. The test elements 31 are arranged at defined intervals via the recesses 30 into which the test elements 31 may be directly inserted, and are to have a defined size and shape in order to fit into the recesses 30. The test elements 31 may be used, for example, to check interval sensors that are arranged on the mobile device. For example, the publication DE 10 2021 210 771 A1 discloses a mobile C-arm x-ray device having a Lidar sensor that is so arranged as to scan at least part of the environment of the device cart and a device section. In order to calibrate such a collision sensor system, use may be made of, for example, two such test elements 31. The position of a Lidar 32 (e.g., arranged on the C-arm x-ray device 1) during such a calibration is shown (see also FIG. 7).

Figure 3:
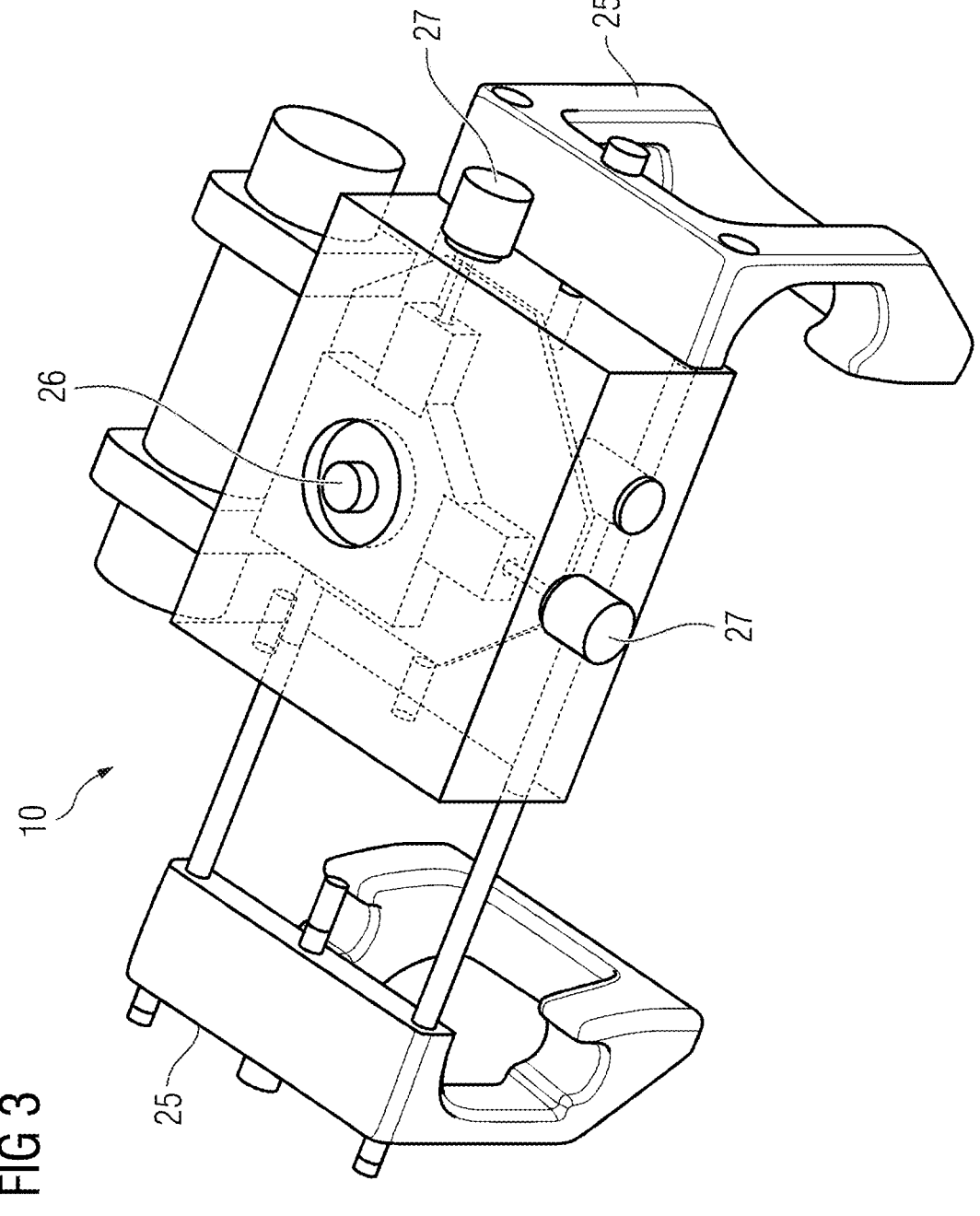
FIG. 3 shows a view of an illumination unit as part of a measuring system for checking the travel accuracy of a mobile device.
Figure 8:
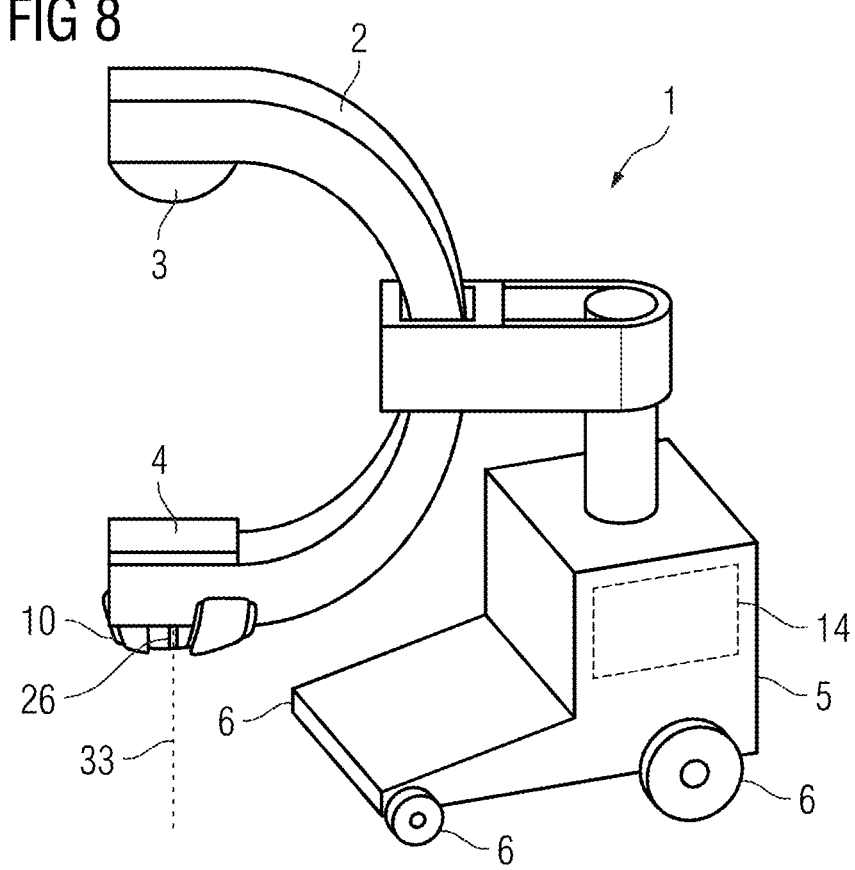
FIG. 8 shows a view of a mobile C-arm x-ray device with an illumination unit arranged thereon.

FIG. 3 shows an illumination unit 10 including a laser 26 (e.g., the corresponding beam is directed downwards in the figure). The laser 26 may be adjusted by setscrews 27. The illumination unit 10 may be arranged on the mobile device by its clamping elements 25 (e.g., on the C-arm of the C-arm x-ray device 1 (see FIG. 8)). In a side view in FIG. 7, only the laser beam 33 radiated from the laser 26 onto the flat mat 7 is shown. For a particularly simple and stable adjustment, the laser beam 33 falls orthogonally onto the flat mat 7. FIG. 8 shows a possible positioning of the illumination unit 10 on the C-arm 2. The control unit 14 is situated on the device cart 5, for example.

In order to perform the method using the measuring system, two preliminary acts are initially to be carried out by a service technician or other operator. The flat mat 7 is first to be constructed (e.g., by joining the mat modules 7.1 together and placing the mat modules 7.1 on the floor). The illumination unit 10 is also to be attached to the C-arm 2 of the C-arm x-ray device 1 (e.g., clamped or bolted on).

Figure 6:
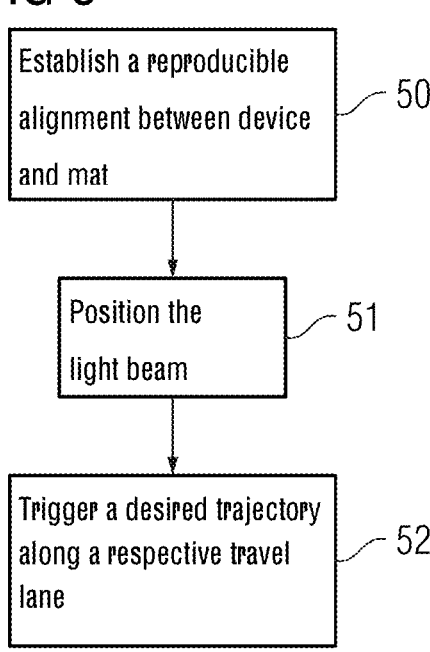
FIG. 6 shows a sequence of acts of a method for checking a travel accuracy of a mobile medical device that may be moved over the floor.

FIG. 6 shows the acts of the method. In a first act 50, the C-arm x-ray device 1 is reproducibly aligned with the mat with respect to position and orientation, such that the respective coordinate systems of the mobile C-arm x-ray device 1 and the flat mat 7 are congruent. This may be performed, for example, using the laser cross 34 of the C-arm x-ray device, which generally serves to set the isocenter. A unit for generating such a laser cross 23 may be present on a C-arm x-ray device 1. The alignment may be performed such that, for example, positioning on the zero point mark 8 is performed using the laser cross 34 and the orientation is set by aligning the laser cross 34 with the x-axis and y-axis.

In a second act 51, the laser beam 33 of the laser 26 of the illumination unit 10 is adjusted (e.g., by the setscrews 27), such that the laser beam 33 is directed precisely onto the zero point mark 8 of the flat mat 7 (e.g., such that the point of incidence is on the zero point mark and the light spot thus generated illuminates the zero point mark 8).

Finally, in a third act 52, the check of the travel accuracy is performed by triggering the mobile C-arm x-ray device 1 to move along the travel lanes 9.1, 9.2.

For this purpose, use is made of, for example, a specially assigned and stored control program that is triggered by, for example, a control unit of the mobile C-arm x-ray device 1. The control program contains control specifications for desired trajectories of the mobile C-arm x-ray device 1 along the travel lanes 9.1, 9.2 of the flat mat 7 from the respective start mark 23 to the respective destination mark 24 (e.g., there only or there and back) over precisely the length that corresponds to the distance between start mark and destination mark 24. It is therefore possible to trigger, for example, a desired trajectory of 50 cm in an x-direction if the length of the straight travel lane 9.1 along the x-axis is 50 cm (e.g., distance between start mark 23 and destination mark), or 80 cm in a y-direction if the length of the straight travel lane 9.1 along the y-axis is 80 cm (e.g., distance between start mark 23 and destination mark 24), and the reverse directions besides. The control program and the travel lanes of the flat mat 7 are coordinated accordingly, such that the control program contains a desired trajectory for each travel lane or at least for each important travel lane. The control program therefore contains at least reference specifications for desired trajectories for two reciprocally orthogonal straight travel lanes in the main directions (e.g., x-axis x and y-axis y, which generally correspond to forwards/backwards and sideways of the mobile device) and for the curved travel lane in a circular path ($\phi$). Corresponding to the flat mat, for example, further desired trajectories (e.g. diagonal movements, movements of various lengths in the same direction, circular paths of various radiuses, etc.) may be provided as desired trajectories that may be triggered. The reference specifications may include one-way journeys and/or pairs of movements in each case. The second movement is an inversion of the first (e.g., there and back) in order to measure both the precision and the accuracy of repetition.

In the context of verifying the travel accuracy, provision is made in the third act 52 for, for example, successively triggering the respective desired trajectories along the two or more straight travel lanes 9.1, beginning at the start mark with the objective of arriving at the destination mark, and possibly in the case of a desired trajectory that goes there and back, with the objective of arriving back at the start mark again. By observation, for example, the operator may monitor the motion of the light spot of the light beam/laser beam in relation to the travel lane. After completion of the respective desired trajectory, the operator then checks where the light spot is situated (e.g., whether the light spot is situated inside or outside the error region 20 of the destination mark (or start mark)). If the light spot of the light beam/laser beam lands outside the error region 20, the travel accuracy is not sufficient. In this case (e.g., using grid patterns or length data from the flat mat 7), an exact deviation may also then be ascertained and measured manually by the operator. This may be performed for the outward journey and the return journey.

The respective desired trajectory along the curved travel lane 9.2 is triggered likewise, beginning at the start mark. Here too, the operator may, for example, monitor the course of travel. Following completion of the desired trajectory, the operator again verifies whether the laser beam is situated inside the error region 20 and, if necessary, the extent of the deviation, not only in relation to the direction but also in relation to the radius of the track. This may be performed easily and precisely by the measuring system including flat mat 7, illumination unit 10, and control program if applicable. Measured deviations may be used for recalibration if the deviations exceed the tolerance range. The manual measurement of deviations by the operator may be performed, for example, using measuring tools such as a folding rule, etc.

Figure 9:
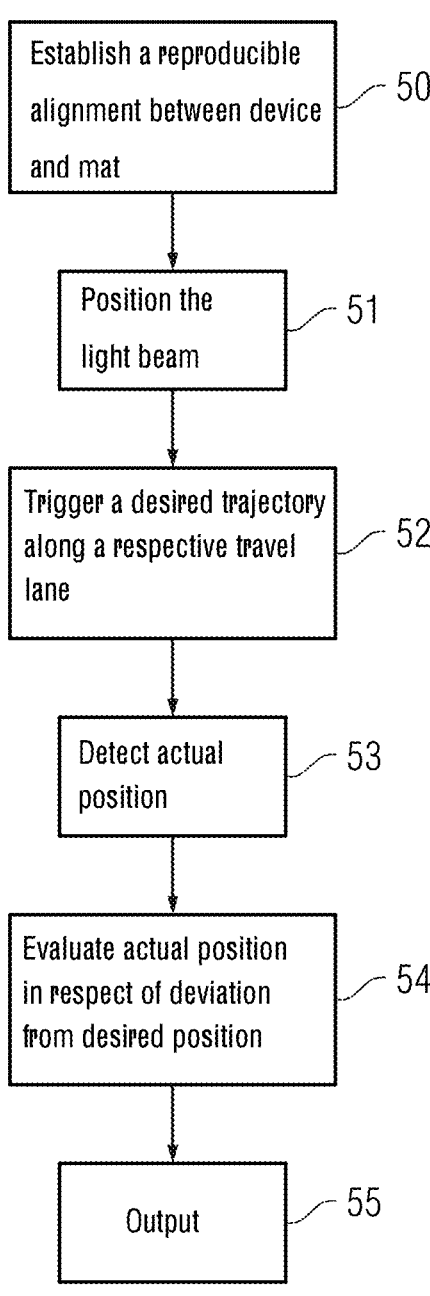
FIG. 9 shows a further sequence of acts of a method for checking a travel accuracy of a mobile medical device that may be moved over the floor.

FIG. 9 shows further acts in addition to the three acts (see FIG. 6). The further acts are performed automatically, for example, instead of the manual check by an operator.

In a fourth act 53, using a detection unit that is arranged, for example, on the illumination unit, the respective actual position of the medical device relative to the indicator pattern (e.g., the travel lanes, etc.) is detected during or after the travel motion of the mobile device. This may be performed once at the end of or following completion of the desired trajectory, or continuously during the travel motion. The detection unit may take the form of, for example, a camera. This records the exact position(s) of the light spot of the light beam/laser beam relative to the track markings or travel lanes (e.g., during the travel motion or at the end thereof). In the simplest case, only the actual position at the end of the travel motion relative to the destination mark is captured.

In a fifth act 54, actual positions detected by the detection unit are evaluated (e.g., by an evaluation unit). The evaluation takes place, for example, with respect to any deviation of the respective actual position from a predetermined desired position. The actual position is represented, for example, by the detected position of the light spot of the light beam/laser beam, and the desired position (e.g., by the destination or start mark or the travel lane). The precise deviation is determined therefrom. The deviation then represents a measure for the travel accuracy of the mobile device. An evaluation may consider merely whether the light spot is situated inside or outside the destination or start mark, or a precise evaluation of the deviation may be effected.

In a sixth act 55, a signal or indication is output based on the evaluation result. This may be effected, for example, visually on a monitor, by an indicator light, or by a microphone. If there is no deviation or if the deviation is below a threshold value (e.g., inside the error region), this may result in, for example, a confirmation sound, a confirmatory (e.g., green) light, or a confirmatory text message. If the deviation exceeds a threshold value (e.g., outside the error region), a warning sound, a warning (e.g., red) light, or a warning text may, for example, be output.

In a further act, if the threshold value for the deviation is exceeded, a recalibration of the control unit with the control program may be indicated and/or performed. Further, the deviations that have been measured or determined may be used for the purpose of calibration.

Via the measuring system and the method, it is possible to verify the travel accuracy without radiation or external measuring systems (e.g., cameras). The use of a flat mat allows a simple mechanical construction that may be broken down in a modular manner into parts that are easy to manage for servicing purposes. The size of the partial mats may be selected such that the partial mats fit into typical cases/boxes that are used in the context of servicing. Via the modular design, it is also possible to extend the flat mat if future functions (e.g., panoramic imaging) require extended travel programs with greater distances. In conjunction with the control program that is assigned to the mat and the illumination unit, the control program being stored on or downloaded onto the control unit of the mobile device, the verification, and/or calibration may be carried out by someone without training on complicated measuring equipment.

The mat may also have light sensors by which the motion of the light beam is detected directly. The measured values that are detected may then be evaluated accordingly.

The present embodiments may be summarized as follows: For a particularly precise check of the travel accuracy, a measuring system is provided for checking and/or calibrating a travel accuracy of a mobile medical device (e.g., a mobile C-arm x-ray device) that may be moved over the floor automatically or semiautomatically in a motorized manner. The measuring system includes a flat mat with an underside that may be arranged on the floor, and with an upper side on which indicator patterns that include at least one zero point mark for positioning the medical device and a number of track markings for travel motions of the mobile device are arranged. The measuring system also includes a unit for illuminating the indicator patterns that are arranged on the mat using at least one concentrated light beam. The unit is arranged on the mobile medical device (e.g., removably), such that the light beam is directed onto the upper side of the mat.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A measuring system for checking, calibrating, or checking and calibrating a travel accuracy of a mobile medical device that is movable over the floor automatically or semiautomatically in a motorized manner, the measuring system comprising:

a flat mat with an underside that is arrangeable on the floor, and with an upper side on which indicator patterns that comprise at least one zero point mark for positioning the medical device and a number of track markings for travel motions of the mobile medical device are arranged; and an illuminator configured to illuminate the indicator patterns that are arranged on the flat mat using at least one concentrated light beam, the illuminator being arranged on the mobile medical device, such that the light beam is directed onto the upper side of the flat mat.

2. The measuring system of claim 1, wherein the illuminator is removably arranged on the mobile medical device.

3. The measuring system of claim 1, wherein the track markings comprise at least three travel lanes, two of the at least three travel lanes being straight travel lanes arranged orthogonally relative to each other and one of the at least three travel lanes being an at least partly curved travel lane.

4. The measuring system of claim 1, wherein each of the at least three travel lanes has at least a start mark and a destination mark.

5. The measuring system of claim 1, wherein the indicator patterns contain coordinate system patterns, grid patterns, dimensional data, error region markings, or any combination thereof.

6. The measuring system of claim 1, wherein the flat mat is assembleable in a modular manner from at least two mat modules.

7. The measuring system of claim 6, wherein the flat mat comprises a number of mat modules that are shaped and assembleable in the manner of a jigsaw puzzle.

8. The measuring system of claim 1, wherein the indicator patterns are formed by dots, lines, circles, segments of a circle, rectangles, or any combination thereof.

9. The measuring system of claim 1, wherein the illuminator takes the form of a laser.

10. The measuring system of claim 4, further comprising a control unit with a control program for triggering travel motions of the mobile medical device on the flat mat.

11. The measuring system of claim 10, wherein the control program is configured to output control specifications for desired trajectories of the mobile medical device along the track markings of the flat mat, and wherein each of the desired trajectories is assigned to a travel lane.

12. The measuring system of claim 11, wherein the control program is configured to output control specifications for desired trajectories of the mobile medical device along the track markings of the flat mat from the start mark to the destination mark of the respective travel lane, back, or a combination thereof.

13. The measuring system of claim 1, further comprising a detection unit configured to detect an actual position of the mobile medical device relative to the indicator patterns.

14. The measuring system of claim 11, further comprising an evaluation unit configured to evaluate the detected position of the mobile medical device relative to the indicator patterns with respect to any deviation of an actual position from a desired position, with respect to any deviation of an actual trajectory from a desired trajectory, or with respect to a combination thereof.

15. The measuring system of claim 1, further comprising an alignment unit that is arranged on the mobile medical device, wherein the alignment unit is configured to align the mobile medical device with the flat mat.

16. The measuring system of claim 1, wherein the flat mat has at least one recess.

17. The measuring system of claim 16, wherein the at least one recess comprises at least two recesses that are arranged at defined intervals and are configured to allow insertion of test elements for the purpose of checking interval sensors that are arranged on the mobile medical device.

18. A method for checking a travel accuracy of a mobile medical device that is movable over a floor using a measuring system, the method comprising:

establishing a reproducible alignment of a coordinate system of a mat with a coordinate system of the mobile medical device, the establishing comprising arranging the mobile medical device on the mat in a predefined position and orientation;

positioning a light beam emerging from an illuminator such that the light beam illuminates a start mark, a destination mark, or the start mark and the destination mark; and triggering at least one desired trajectory using a control unit with a control program, such that the mobile medical device is moved along a travel lane that is assigned to a desired trajectory of the at least one desired trajectory.

19. The method of claim 18, further comprising:

detecting actual positions of the mobile medical device relative to the indicator pattern at least at an end of the desired trajectory;

evaluating the actual positions that have been detected, with respect to any deviation from a predetermined desired position, the respective deviation representing a measure of the travel accuracy of the device; and outputting a signal or an indication based on the evaluating.

20. The method of claim 19, further comprising indicating, performing, or indicating and performing a recalibration of the control unit with the control program when a threshold value for the respective deviation is exceeded.

* * * * *